(12) United States Patent
Andersen

(10) Patent No.: US 6,581,293 B1
(45) Date of Patent: Jun. 24, 2003

(54) DEVICE IN CONNECTION TO HOLE PUNCHING PLIERS ARRANGED TO PUNCH HOLES IN A SKIN PROTECTION PLATE FOR STOMA BAG

(76) Inventor: Svein Jakob Andersen, Opalveien 15, N-4070 Randaberg (NO)

( * ) Notice: Subject to any disclaimer, the term of this patent is extended or adjusted under 35 U.S.C. 154(b) by 0 days.

(21) Appl. No.: 09/914,960
(22) PCT Filed: Mar. 2, 2000
(86) PCT No.: PCT/NO00/00077
§ 371 (c)(1), (2), (4) Date: Jan. 18, 2002
(87) PCT Pub. No.: WO00/51533
PCT Pub. Date: Sep. 8, 2000

(30) Foreign Application Priority Data

Mar. 4, 1999 (NO) .......................... 19991084

(51) Int. Cl.$^7$ ................................ B25B 7/22
(52) U.S. Cl. ............................ 30/363; 30/349; 30/177; 30/186; 30/244; 30/301; 83/905
(58) Field of Search .......................... 30/349, 177, 186, 30/244, 301; 83/905

(56) References Cited

U.S. PATENT DOCUMENTS

| 732,030 | A | * | 6/1903 | Allen ........................... 30/363 |
| 4,235,073 | A | * | 11/1980 | Tracy ............................ 59/11 |
| 4,858,317 | A | * | 8/1989 | Seib et al. ..................... 30/115 |
| 5,052,258 | A | * | 10/1991 | Hunter ......................... 83/589 |
| 5,377,415 | A | | 1/1995 | Gibson |
| 5,398,718 | A | * | 3/1995 | Roinick, Sr. ................. 137/318 |
| 5,472,115 | A | * | 12/1995 | Whiton ........................ 221/25 |
| 5,722,563 | A | * | 3/1998 | Hunts ........................... 83/628 |

* cited by examiner

Primary Examiner—Allan N. Shoap
Assistant Examiner—Phong Nguyen
(74) Attorney, Agent, or Firm—Knobbe Martens Olson & Bear LLP

(57) ABSTRACT

A pair of hole punching pliers, so-called stoma pliers, is arranged to punch a hole in a skin protection plate for a stoma bag. The hole punching remedies of the pliers consist of a hole socket (16) and a holding-up plate (18) for the same. During the punching, a plastic skin protection plate is located between the hole socket (16) and the opposing surface of the holding-up plate (18), as the free, outer cutting/punching edge (22) of the hole socket (16) after the completion of the punching abuts directly on said opposing holding-up plate surface. To achieve an optimal punching operation, which is dependant upon the hole socket's (16) outer punching edge part (22) being placed maximally perpendicularly on said holding-up plate surface, at the same time as this surface should be able to dislocate (turning eccentrically) in relation to the wearing effect of said outer punching edge part on the surface of the holding-up plate by its abutments against same at the completion of each hole punching, at least the hole socket (16) has pivotal bearing around a lateral axis (24), which is arranged perpendicularly on its symmetrical axis (26), which in its closed position at the completion of each hole punching runs eccentrically in relation to the symmetrical axis (30) of the holding-up plate (18), which said symmetrical axis forms the pivotal axis of the holding-up plate (18).

6 Claims, 5 Drawing Sheets

DEVICE IN CONNECTION TO HOLE PUNCHING PLIERS ARRANGED TO PUNCH HOLES IN A SKIN PROTECTION PLATE FOR STOMA BAG

The present invention concerns a device connected to hole punching pliers, which are arranged to punch holes in a protective plate for a stoma bag, and where the nose of the pliers is equipped with co-operating hole punching remedies in the shape of a hole socket and a holding-up plate for said socket.

A considerable number of the population, approximately 4% or a good 13000 persons in Norway alone, are in a situation of having been stoma operated and having to live with laid out intestine. The remedy used by a stoma operated person to handle the feces from the intestine end, which has been laid out from the body, is a stoma bag. The bag is secured to the body by means of a skin protecting plate where holes have been made to introduce the intestine end into the bag. The plate is fitted with a glue part on the skin side, so that it may be secured to the body. The size of each individuals intestine end will vary with time, meaning the hole has to be constantly changed. The difference is normally between 1 and 3 mm. Likewise, the size of the intestine differs form person to person.

Thus, the plate may not be fitted with a uniform opening for the intestine end. The individual may also not use plates having identical holes, as the size of the intestine may have altered once the plate has to be changed. Some persons change plate and bag as often as 1–3 times daily, while for others 2–3 weekly changes may be sufficient. The difference in intestine size is assumedly the reason why the suppliers promoting bags and plates prescribe the hole be cut with scissors.

In practice it turns out that the cutting of holes with scissors leads to great disadvantages to most users. One disadvantage is due to the fact that the plate is relatively thick in the area where it is to be cut, meaning the hole will have a jagged edge and accordingly not fit tightly enough around the intestine end.

The feces are cauterizing and cause discomfort, especially sore skin, if an uneven cut leads to skin coming into contact with feces. It is therefore not unusual that several plates have to be cut before an acceptable result is achieved. Alternatively, the leaks around the intestine end, resulting from an unevenly cut hole, may be sealed by means of a paste.

As it is impossible to control the defecation, it is preferable that the changing of plate and bag be as rapid as possible.

Before a new bag and plate can be fitted, the intestine has to be controlled for size, which can first be effectuated after the removal of the used bag and plate. It is thus hard to avoid contact between feces and naked skin or clothing, especially when knowing that the most experienced users need up to 10 minutes to cut a suitable hole. Elderly users may have trouble with the cutting.due to shaking hands etc. The hole may also not be cut to fit too tightly, as it causes discomfort when the intestine end is squeezed. Moreover, many users feel mental unease caused by the dread of the discomfort of a wrongly adjusted hole.

As it is not unusual that 2–3 plates have to be cut before the hole is as required, it is evident that the cutting also has unwanted economic results.

It is true that pliers based on hole punching operations carried out more or less in one operation, instead of cutting, are known, cf. e.g. U.S. Pat. No. 4,817,287. These known hole punching pliers are generally constructed as a pair of scissors having two elements which are pivotally connected to each other by means of a cross member, and where the two parts of the pivotal elements positioned on one side of the member create handles, while the free ends of the element parts on the other side of the member carry a so-called hole socket and a holding-up plate for the hole socket at their free end, as the punching of holes in a suitable plastic material for the skin protection plate obviously takes place with this placed between the hole socket and the holding-up plate.

In these known hole making pliers the hole socket, as well as the holding-up plate are secured to the end of the respective pivotal pliers. In such a constructive embodiment of the hole making pliers one pair of pliers is needed for each hole dimension.

It is furthermore a disadvantage concerning these known hole making pliers that the hole socket and the holding-up plate have to be dimensioned with precision and placed very accurately in relation to each other to achieve that the free working edge circumference of the hole socket hits the opposed surface of the holding-up plate as perpendicularly as possible, thus to secure cleanly cut hole edges in the skin protection plates of the stoma bags.

Concerning the above described known hole making pliers, an embodiment is shown in which a circumferential slot is formed in the holding-up plate, being nearly complementarily shaped to the outer, free cutting edge part of the hole socket. Also in other embodiments of the pliers, of this and similar natures,—having one and the same dimension of pliers—the free cutting edge of the hole socket will hit the opposed surface of the holding-up plate almost identically with every hole making operation, so that the holding-up plate is constantly worn in the same place, and is damaged.

The scope of the invention has i.a. been to remedy, or to a substantial degree reduce, the defects, the disadvantages and the limitations of application in known techniques, and thus provide a pair of hole punching pliers where the necessary measures are taken, partly to facilitate an exchange of hole sockets having different diameters, partly to secure correct adaptation between hole socket and holding-up plate during each hole punching operation, and partly to postpone damaging wear on the holding-up plate, thus providing it with an extended useful duration.

To realise the above mentioned scope, the invention distinguishes itself in the features designated in the characterizing clause of claim 1.

According to the invention the hole socket and/or the holding-up plate are placed restrictedly pivotally around separate axes stretching perpendicularly on the symmetrical axis of the hole socket, respectively of the holding-up plate. This secures the correct adaptation of the free cutting/punching edge area of the hole socket in relation to the opposed holding-up surface, that is, with said free cutting edge area directed perpendicularly towards said holding-up plate surface, with the intermediate skin protection plate.

To distribute the wear from the free cutting edge of the hole socket onto the holding-up plate, it is convenient for the holding-up plate to have a freely pivotal bearing around an axis which runs parallel to its symmetrical axis, and eccentrically in relation to the symmetrical axis. Thus the abutment of the outer, free cutting edge of the hole socket on the holding-up plate will relocate from one hole punching operation to the next, so that the said wear will be distributed over the holding-up plate.

The fact that the holding-up plate is freely pivotal also means that users who do not possess the strength required to push the hole socket through the skin protection plate, may rotate the holding-up plate once the pliers are squeezed, and may thus achieve a cutting effect.

A non-limiting example of preferred embodiments are explained below with reference to the accompanying illustrations, where:

FIGS. 1 and 2 show a first embodiment of a pair of stoma pliers shaped according to the invention, while FIGS. 3–5 show a second embodiment where FIG. 1 shows a side view of the stoma pliers in open position;

FIG. 2, which corresponds to FIG. 1, shows the stoma pliers in closed position;

FIG. 3 corresponds to FIG. 1, but shows a second embodiment which in particular concerns the bearing of the holding-up plate, which is shown in cross section, together with the outer part of the hole socket;

Figure 1:
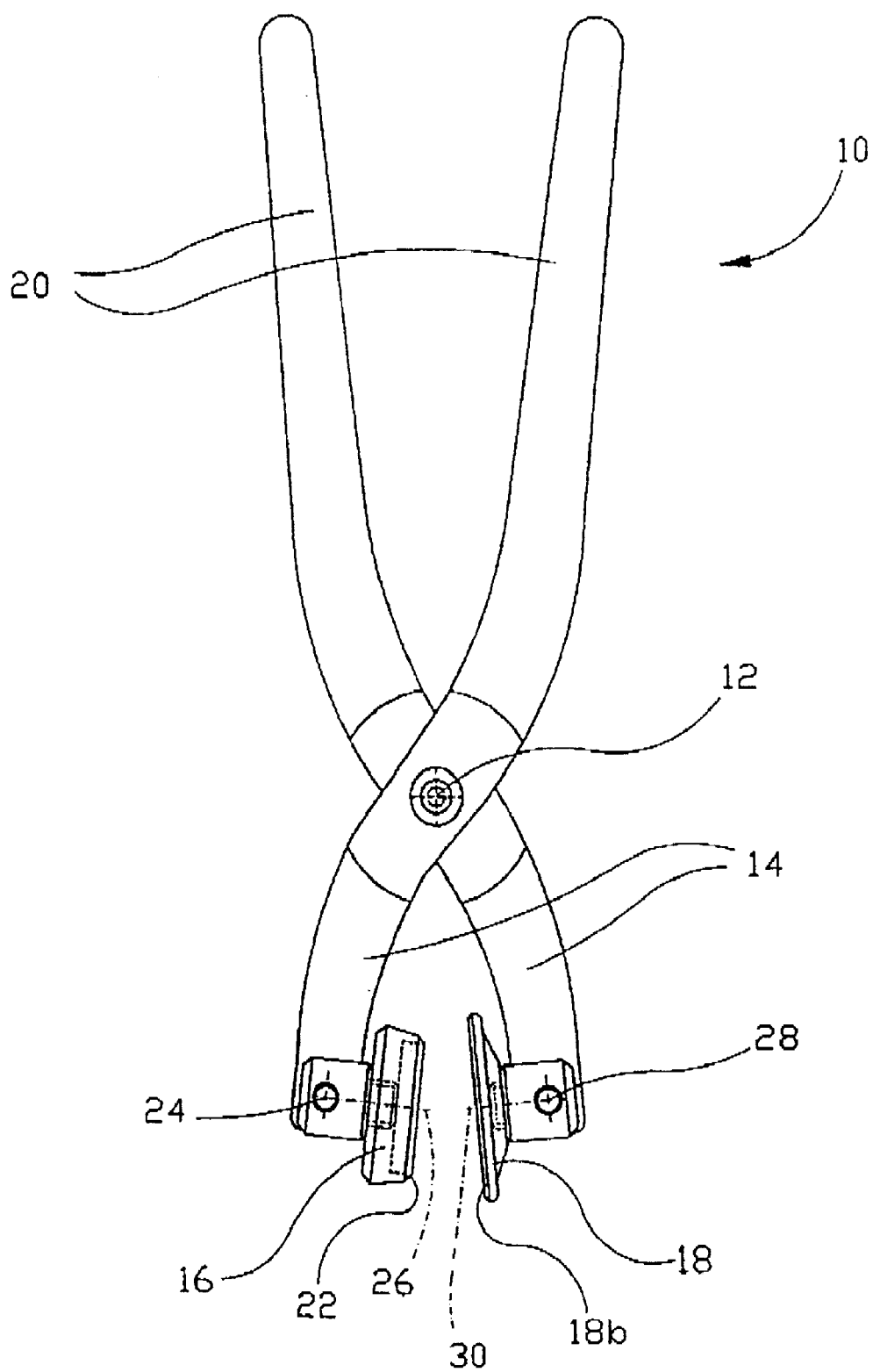
Figure 2:
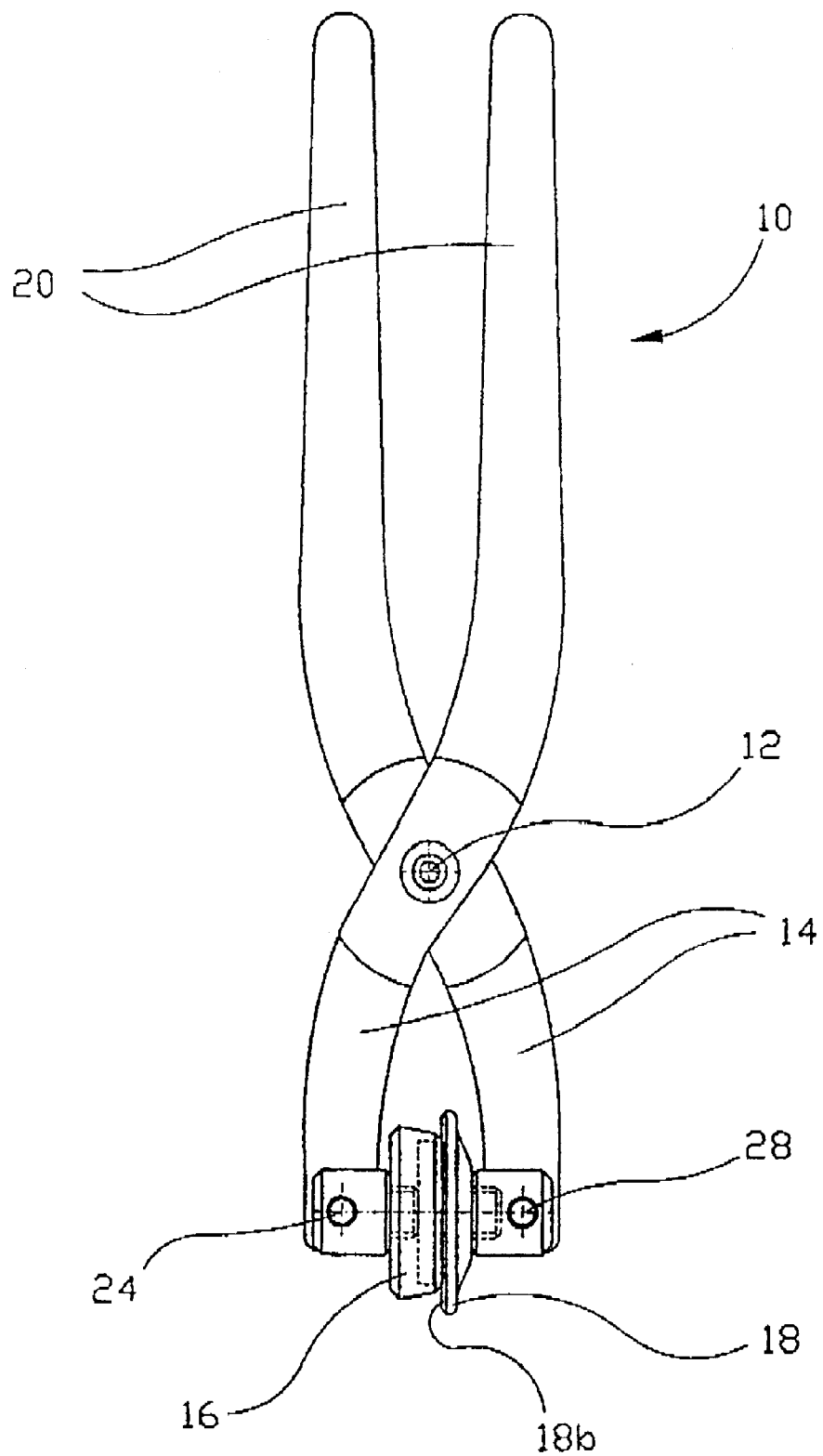

We firstly refer to FIGS. 1 and 2, in which the number of reference 10 generally indicates a pair of so-called stoma pliers, whose parts are denoted by 12.

Partly, a so-called hole socket (cutting head) 16 is pivotally arranged to the free ends of the pliers' nose, partly a holding-up plate 18 for the hole socket 16 is arranged to said free ends. On the surface facing the hole socket 16 the holding-up plate is equipped with a thin layer of plastic material 18b. In a plastic skin protecting plate (not shown), belonging to a stoma bag (also not shown), a hole will be punched to facilitate the introduction of the intestine end into the stoma bag. As the size of the intestine end will vary with time for each patient, the hole dimension has to be altered frequently.

This may be performed in the known way by inserting the skin protection plate between hole socket 16 and holding-up plate 18 in the position shown in FIG. 1, and then by a normal squeezing movement of the pliers' handles 20 to bring together hole socket 16 and holding-up plate 18 with the intermediate plastic plate 18b, whereby the sharp, free, peripheral cutting/punching edge 22 of the hole socket 16 cuts through said skin protection plate making a hole in it, which corresponds to the circumferential shape of said cutting/punching edge 22. The punching process is completed when the outer, free cutting/punching edge 22 of the hole socket abuts on the opposed surface of the holding-up plate 18b, without any intermediate plastic material from the skin protection plate. Both the hole socket 16 and the holding-up plate 18 are screwably connected to each respective end of the pliers' nose 14, so that they may easily be replaced for another dimension.

In order to achieve optimal adaptation between hole socket 16 and holding-up plate 18, at least one of these hole punching remedies 16, 18 has pivotal bearing around an axis which is perpendicular on the symmetrical axis of the respective hole punching remedy (16, 18).

According to the embodiment according to FIGS. 1 and 2 the hole socket has thus a bearing around a lateral axis 24, which is perpendicular on the symmetrical axis 26 of the hole socket 16. In a corresponding way the holding-up plate 18 has a bearing around a lateral axis 28 which is perpendicular on the symmetrical axis 30 of the holding-up plate 18.

In addition to optimising the adaptation between the hole punching remedies, whereby the hole socket 16 enters into hole punching position with its cutting/punching edge 22 directed perpendicularly onto the skin protecting plate (not shown), which abuts on the holding-up plate during the hole punching operation, the pivotal bearing of the hole punching remedies 16 and 18 in addition facilitates the simple replacement of the respective remedy.

Figure 3:
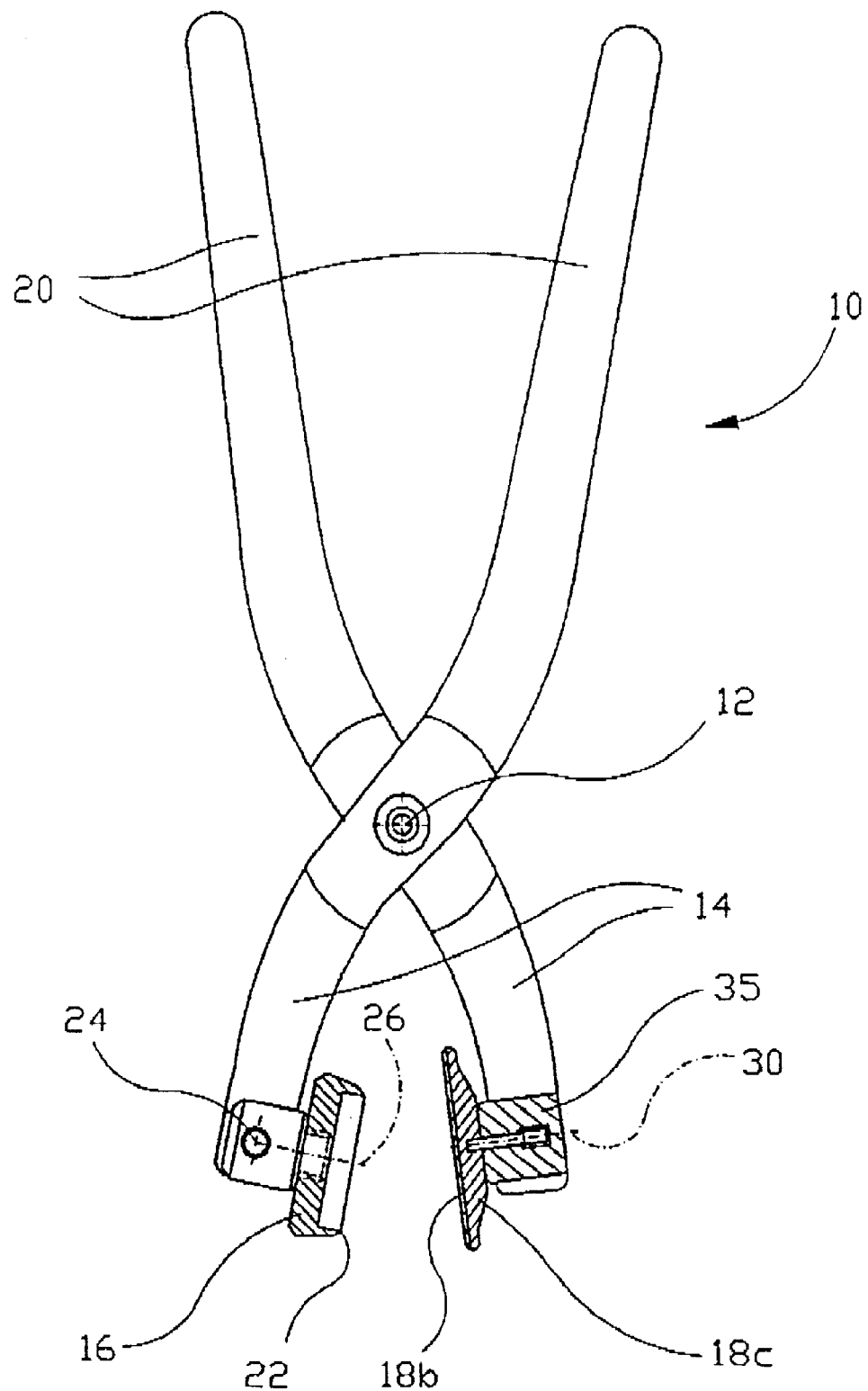
Figure 4:
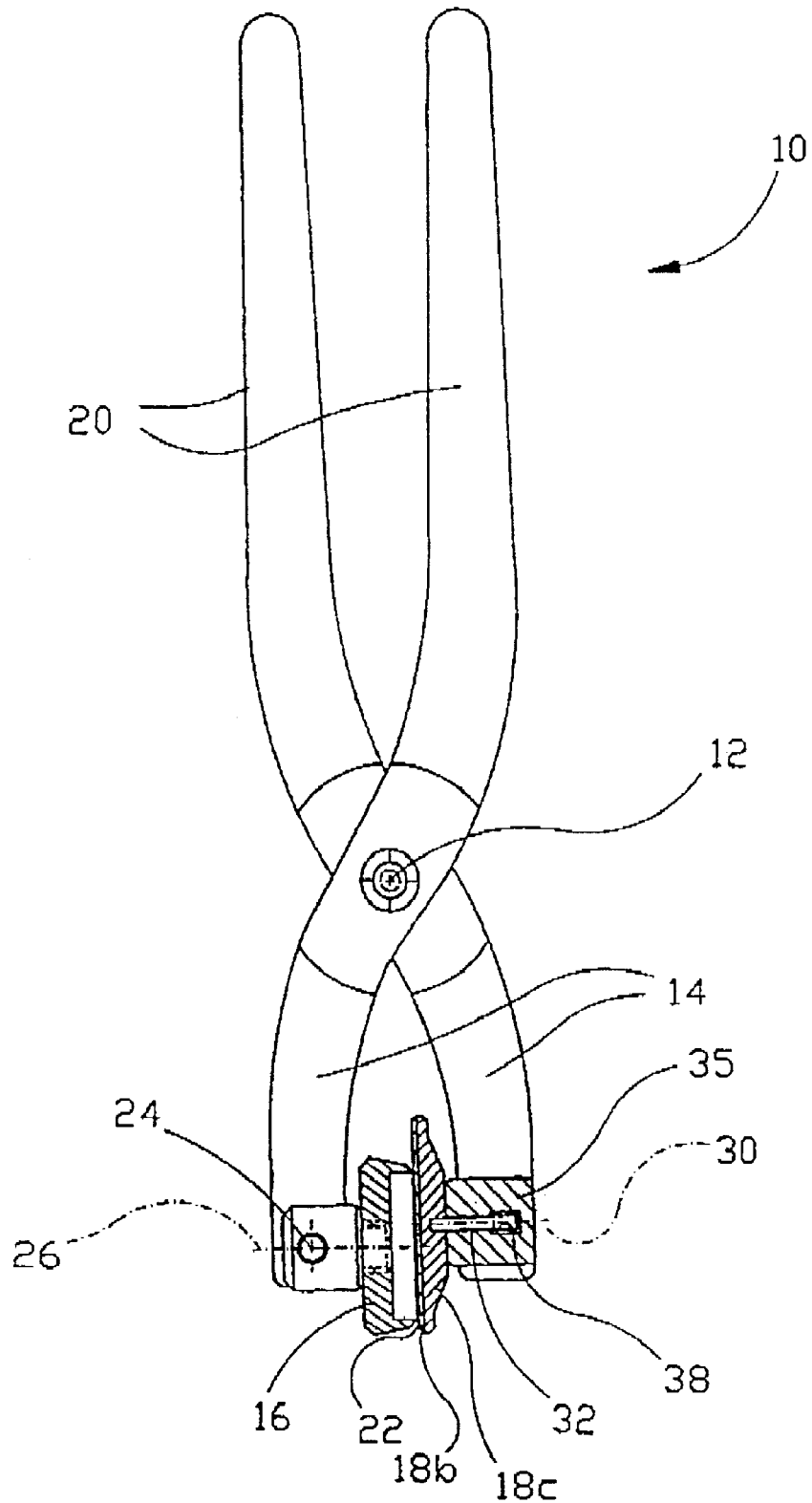
FIG. 4 shows the stoma pliers of FIG. 3 in closed position.
Figure 5:
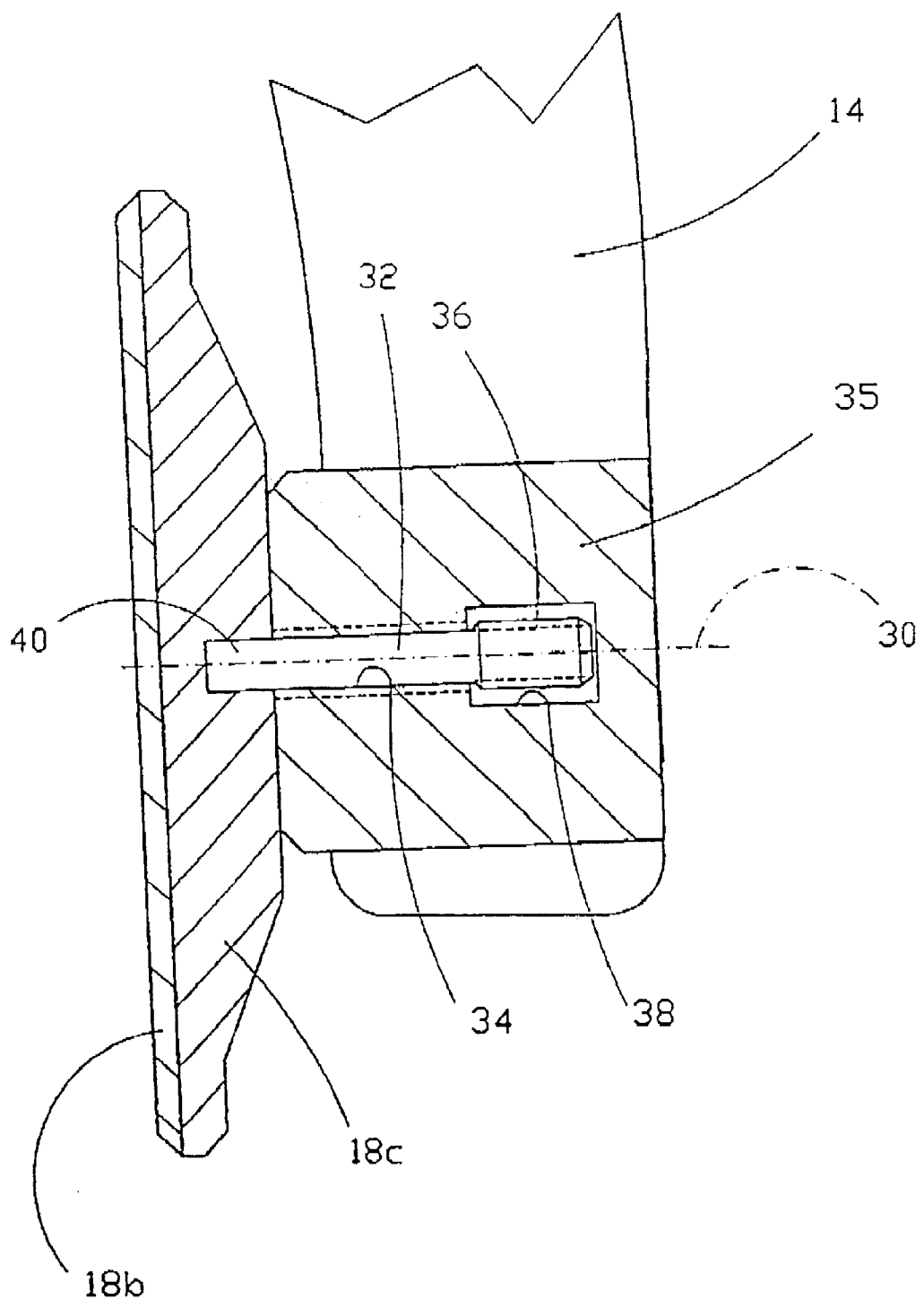
FIG. 5 is sketch of a sectional view on a larger scale, showing the bearing of the holding-up plate.

The embodiment according to FIGS. 3–5 substantially corresponds with the embodiment shown in FIGS. 1 and 2, except for the bearing of the holding-up plate 18. Concerning parts of the two embodiments which are identical or functionally similar, the same numbers of reference are used. For the holding-up plate, which in FIGS. 3–5 has a different bearing and correspondingly deviating function in relation to the holding-up plate 18 of FIGS. 1 and 2, the indicating reference 18c is used.

In the embodiment according to FIGS. 3 and 4, it is only the hole socket 16 which has pivotal bearing around a lateral axis 24 perpendicularly on its symmetrical axis 26. With regard to the mentioned orientational adaptation between the hole punching remedies, the hole socket 16 and the holding-up plate 18c, it is as mentioned sufficient that one of these remedies, e.g. the hole socket 16 (or the holding-up plate 18c) performs this pivotal ability in relation to the other remedy.

The holding-up plate 18c in the, embodiment according to FIGS. 3–5 has a symmetrical axis 30 running eccentrically with regard to the corresponding axis 26 of the hole socket in the hole punching position.

Moreover, the holding-up plate has pivotal bearing around this symmetrical axis 30. This is effected by a bolt 32 being screwed through an internally threaded boring 34 in one in the pliers nose part 14 inserted block-like part 35, FIG. 5, with its short externally threaded end part 36, which after the screwing-in of the bolt 32 in the boring 34 has ended in an unthreaded cavity 38. The opposite part 40 of the bolt 32 is secured in a known way to the holding-up plate 18a, which is fitted with an overlaying glued-on or otherwise attached holding-up plate 18b.

When the holding-up plate 18b, 18c is pivotal around an axis 30 which is eccentric in relation to. the axis of the hole socket 16, will the circular abutment of the hole socket 16 against the holding-up plate 18b, through the latter's mutually deviating pivotal positions in relation to the hole socket 16 from one punching operation to the next, be unevenly distributed over that holding-up plate surface which during the punching is facing the peripheral cutting/punching edge of the hole socket.

To facilitate potential turning of the holding-up plate 18, 18c simultaneously with the squeezing together of the pliers, the periphery of the holding-up plate may be fluted or serrated.

What is claimed is:

1. Hole punching pliers for punching holes in a skin protection plate for a stoma bag, the pliers comprising:
   a first plier part;
   an intermediate member;
   a second plier part pivotably connected to the first plier part directly and solely via the intermediate member wherein the first and second plier parts each have handle portions positioned on a first side of the intermediate member and working portions positioned opposite the handle portions;
   a rotationally symmetric punch having a circumferentially continuous cutting edge arranged in one plane substantially perpendicular to the axis of symmetry of the punch, the punch being attached to the working portion of the first plier part; and
   a counterplate having a symmetry axis and a generally planar face, the counterplate being attached to the working portion of the second plier part wherein at least one of the punch and the counterplate are pivotally attached to the working portion of the corresponding plier part so as to define at least a first lateral axis wherein the at least first lateral axis is arranged to be substantially perpendicular to the axes of symmetry of the punch and the counterplate and wherein operation of the handle portions of the first and second plier parts induces the punch and the counterplate into contact so as to punch a hole in the skin protection plate positioned therebetween, said punch being free to pivot during operation of said pliers.

2. The pliers of claim 1, wherein the counterplate is rotable about the axis of symmetry of the counterplate and wherein the axis of symmetry of the counterplate is disposed eccentrically with respect to the axis of symmetry of the punch when the punch abuts immediately the counterplate.

3. The pliers of claim 1, wherein the counterplate comprises a pivot bearing.

4. The pliers of claim 3, wherein the pivot bearing is secured to the counterplate along the axis of symmetry of the counterplate by a bolt secured against axial movement at a first end of the bolt by a head part and at a second end of the bolt by an externally threaded portion wherein the threaded portion is threadedly connected to the working portion of the second plier part.

5. Hole punching pliers comprising:

first and second plier arms each having a first end and an opposite second end;

a pivot pin interconnecting the first and second plier arms in a pivotable manner;

a punch member defining a cutting plane attached to the first end of the first plier arm; and a backingplate defining a backing plane attached to the first end of the second plier arm wherein actuation of the second ends of the plier arms induces the punch member and backingplate into contact and wherein the punch member and backingplate are pivotably arranged with respect to each other such that the cutting plane and the backing plane are maintained in parallel orientation upon contact of the punch member and the backingplate with material positioned therebetween, said backing plate and said punch being free to rotate during operation of said pliers.

6. The pliers of claim 5, wherein the rotation axis of the backingplate is displaced with respect to the punch member such that rotation of the backingplate changes the region of the backingplate that the punch member contacts.

* * * * *